(12) United States Patent
Abraham et al.

(10) Patent No.: US 6,275,291 B1
(45) Date of Patent: Aug. 14, 2001

(54) MICROPOLARIMETER AND ELLIPSOMETER

(75) Inventors: Michael Abraham, Mainz; Matthias Eberhardt, Lörzweiler, both of (DE)

(73) Assignee: NanoPhotonics AG, Mainz (DE)

( * ) Notice: Subject to any disclaimer, the term of this patent is extended or adjusted under 35 U.S.C. 154(b) by 0 days.

(21) Appl. No.: 09/397,568

(22) Filed: Sep. 16, 1999

(30) Foreign Application Priority Data

Sep. 16, 1998 (DE) .................................... 198 42 364

(51) Int. Cl.[7] .................................................. G01J 4/00
(52) U.S. Cl. .......................... 356/367; 356/364; 356/368; 356/369; 359/489; 359/494
(58) Field of Search .................................. 356/364, 365, 356/366, 367, 368, 369, 33, 34, 35; 359/489, 496, 497; 250/225

(56) References Cited

U.S. PATENT DOCUMENTS

| | | | |
|---|---|---|---|
| 4,158,506 | * 6/1979 | Collett | 356/365 |
| 4,286,843 | 9/1981 | Reytblatt . | |
| 5,166,752 | 11/1992 | Spainer et al. . | |
| 5,416,324 | * 5/1995 | Chun | 250/341.3 |
| 5,502,567 | * 3/1996 | Pokrowsky et al. | 356/367 |
| 5,519,493 | * 5/1996 | Reiley | 356/367 |
| 5,548,427 | * 8/1996 | May | 359/73 |
| 5,706,212 | * 1/1998 | Thompson et al. | 356/368 |
| 5,877,859 | * 2/1999 | Aspnes et al. | 356/364 |

FOREIGN PATENT DOCUMENTS

| | | |
|---|---|---|
| 195 47 553 | 3/1997 | (DE) . |
| 197 08 036 | 9/1998 | (DE) . |
| WO 86/07631 | 12/1986 | (WO) . |

* cited by examiner

*Primary Examiner*—Frank G. Font
*Assistant Examiner*—Sang H. Nguyen
(74) *Attorney, Agent, or Firm*—Hudak & Shunk Co., L.P.A.

(57) ABSTRACT

A micropolarimeter and ellipsometer for obtaining complete optical information of superficially illuminated specimens. A compact construction is designed to facilitate their use. To obtain the simultaneous surface measurement of all optical information from a specimen, the retarder of the micropolarimeter consists of a one-piece retarder array with at least one pixel group, in which the major axis orientations of the individual pixels are distributed over an angular range of 360°. This micropolarimeter can be integrated into the reflected light microscope of an ellipsometer. The result is a compact measurement unit.

15 Claims, 6 Drawing Sheets

MICROPOLARIMETER AND ELLIPSOMETER

BACKGROUND OF THE INVENTION

This invention relates to a micropolarimeter with a retarder, an analyzer disc located downstream of that and a photo-detector matrix as well as an ellipsometer with a light source, polarizer and polarimeter and to an ellipsometer with a light source, polarizer, polarimeter and reflected light microscope with lens and eyepiece, whereby the polarizer and polarimeter are integrated into the reflected light microscope.

In industrial applications, light is frequently used as a contactless probe to measure the characteristics of a specimen. The change in the properties of the beam following interaction with the specimen is used to make the evaluation. Polarimetry and ellipsometry use the information contained in the polarization characteristics and the changes in that information as a result of the interaction with the specimen. In fully polarized light, these characteristics are the ellipticity, the position of the major axis in three dimensions (azimuth) and the direction of rotation of the field strength vector. For partly polarized light, the degree of polarization is also included. These variables are described by the four elements of the Stokes vector which are designated the Stokes parameters (see R. M. Axxam, Bashara, Ellipsometry and Polarized Light, North Holland, Amsterdam, 1988).

Devices for the measurement of the parameters of polarized light are called polarimeters. The combination of a polarized light source with a polarimeter for the measurement of the characteristics of thin films and surfaces is called an ellipsometer. From the basic ellipsometric variables, and by using appropriate mathematical algorithms, it is possible to calculate the characteristics of the specimens, such as the thickness and the refractive index of films. To obtain information on the characteristics of the specimen at different locations on the specimen, the specimen is conventionally moved by a displacement device.

Information of this type is of great significance for quality control in the thin film and microelectronics industries. In the glass industry, a polarimeter can be used to analyze the stresses in a sheet of glass. As the diameter of the specimens increases, however, the scanning of the surface with an ellipsometer or polarimeter that takes only spot measurements becomes a very time-consuming process. The precision movement of very large specimens also requires to good deal of effort.

In ellipsometry and polarimetry, systems that contain mechanically moved polarizers or retarders (e.g. $\lambda/4$ wafers) are frequently used (see R. M. Axxam, Bashara, "Ellipsometry and Polarized Light", North Holland, Amsterdam, 1988).

A light source delivers a collimated bundle which is linearly pre-polarized by means of a polarizer. The polarization of the beam changes as a result of its interaction with the specimen. This change can be detected photometrically by means of a retarder and a downstream analyzer with a detector. For this purpose, either the retarder or the analyzer is rotated and the timed periodic signal that occurs is evaluated (see FIG. 1). Such an ellipsometric system supplies the information only for the area of the specimen that is measured in the detection channel. This method is very slow and requires the use of very precise and expensive mechanical tables for the displacement of the specimen.

DE 197 08 036 describes an ellipsometric microscope that combines the construction of a reflected light or even a transmitted microscope with the construction of an ellipsometer, and thereby makes it possible to obtain a direct image of a surface, and simultaneously to evaluate the light reflected by the specimen in terms of polarization and intensity. For this purpose, movable ellipsometer components are used. In particular the procedure attempts to achieve the highest possible lateral resolution for a given angle of incidence between 0° and approximately 90°.

WO 86/07631 describes a photopolarimeter for the simultaneous measurement of all four Stokes parameters, in which three detectors are used for the analysis. In this system, of course, there are no moving parts, and only one point of the specimen is imaged.

U.S. Pat. No. 5,335,066 describes a similar device without moving parts.

EP 0 632 256 A1 describes an array polarimeter. In this case, however, the elements of the array are used for the determination of the polarization characteristics of a measurement beam that images only one point of the specimen.

U.S. Pat. No. 5,166,752 uses a CCD array in an ellipsometric system. The purpose of this system is to use upstream optics to measure a range of different angles of incidence simultaneously, and thus to increase the number of independent measurements for a given point on the specimen.

There is no provision for the simultaneous surface measurement of the polarization characteristics.

DE 195 47 553 C1 describes a device that does not have any moving components, and which, for the simultaneous determination of the polarization status of the electromagnetic beam, has a detector which has fields that are arranged in a matrix-like manner. Polarization films that have different azimuths are attached to the matrix fields of the CCD matrix of the detector. For example, three polarizers with different azimuths are combined into one image element, which corresponds to three angular positions of a rotating analyzer.

A similar system with polarization pixels is described in U.S. Pat. No. 4,286,843. Although a simultaneous measurement of the surface of the specimen is possible, the disadvantage of these systems is that they are very difficult to use in practical terms. The reason for the difficulty is the size of the pixels of the associated photo-detector array, which is in the magnitude of micrometers. The dimensions of these pixels are typically in the range of 20×20 $\mu m^2$. The manufacture of such small pieces from a polarizer film that is typically 300 $\mu m$ thick and their installation on the detector array is a technically very difficult and very expensive procedure. In fact, the author is unaware of any industrial realization of the system described in U.S. Pat. No. 4,286,843. An additional disadvantage is the design of the system in the form of a polarizer array. Thus not all of the Stokes parameters can be determined. In particular, it remains impossible to determine the direction of rotation of the polarization.

SUMMARY OF THE INVENTION

The object of the invention is therefore to create a compact, simultaneously operating imaging micropolarimeter for the simultaneous superficial determination of the film and geometric characteristics of a specimen, whereby the compact size of the system makes it easy to use in process equipment and in ellipsometers. The object of the invention also relates to a compact ellipsometer, by means of which the characteristics of the specimen can be measured easily.

This object is accomplished with a micropolarimeter in which the retarder is a one-piece retarder array with at least one pixel group that has at least three pixels, the major axis orientations of which are distributed over an angular range of 360°. In this case, it is logical to distribute the major axis orientations uniformly over the entire angular range.

The invention teaches that the simulation of the rotation of the retarder can be replaced by an array of retarder pixels that can be read by means of a photo-detector matrix, in particular by means of a CCD camera. Each pixel thereby corresponds to an angular position of the retarder. The polarization characteristics of the pixels in the group vary from pixel to pixel such that from the totality of the photometric information, the polarization of a partial beam of light striking this pixel group can be determined The number of pixels necessary for the polarization analysis is combined into a pixel group, which thereby forms a micropolarimeter.

The advantage of the system of retarder pixels claimed by the invention over systems of polarization pixels of the prior art is that the retarder technique delivers all of the Stokes parameters, and not only 3 of the 4 Stokes parameters.

The retarder array claimed by the invention is a one-piece component, which means that it is no longer necessary to assemble individual pixels. The micropolarimeter can thereby be manufactured economically.

To manufacture a one-piece retarder array, preferably lithographic, embossing or injection molding methods are used. The term "lithographic methods" as used in this application refers to a combination of high-resolution lithography methods with coating and etching techniques. It thus becomes possible for the first time to realize such a retarder array on an industrial scale. The result is a unit that supplies an extremely high information density that cannot be achieved by the prior art either industrially or economically.

In the technologically increasingly important UV range of the spectrum, retarders have significant advantages over film polarizers, the efficiency of which is diminished somewhat in this range. The reason is that retarders like the one taught by the invention can be made of materials that still have a very good transparency in the UV range, e.g. calcium fluoride. On the other hand, film polarizers are made of organic materials, the dichroism of which, which is what gives them their polarization action, diminishes in the UV range.

The pixels of a pixel group are preferably located in at least one pixel line. Such a linear retarder array corresponds to the complete rotation of a conventional retarder. If one point of the specimen is imaged on such an array, the specimen characteristics can thereby be determined on this point without rotation of a retarder.

The retarder array is advantageously a pixel matrix with identical pixel lines. If identical pixel groups are combined in this manner to form a matrix, it becomes possible to obtain additional information. While the X-direction (direction of the pixel line) is used for the polarization analysis, the Y-direction is available for a spectral or angular dispersion. It thereby becomes possible to increase the variety of physical information that can be determined for each specimen point. For example, even multiple-layer systems with a plurality of unknowns can thereby be characterized.

A prism or a grid for a wavelength selection is advantageously located between the specimen and the retarder array.

In an additional embodiment, the pixels of a pixel group are advantageously arranged two-dimensionally. Each pixel group forms a micropolarimeter, whereby the pixel groups can be combined into a matrix that provides an image of the optical characteristics of the specimen.

The pixels preferably consist of dielectric grid structures with grid intervals that are less than the wavelength of the light being used.

Preferably, sub-wavelength structures are used, which are dielectric grid structures, the dimensions of which are significantly less than the wavelength of the light being used.

The size of the detector pixels preferably equals the size of the retarder pixels.

The pixels of the retarder array are preferably located on a common substrate.

The one-piece retarder array is preferably attached to an analyzer wafer by means of adhesive.

The analyzer wafer can in turn be attached to the photo detector matrix by means of adhesive.

The ellipsometer has a reflected light microscope and a micropolarimeter, whereby the polarizer and the micropolarimeter are integrated into the reflected light microscope. The micropolarimeter is located in the focal plane of the eyepiece and has a retarder, an analyzer disc located downstream of it and a photo-detector matrix, whereby the retarder is a one-piece retarder array with at least one pixel group that has at least three pixels, the major axis orientations of which are distributed over an angular range of 360°. The result is a measurement device that is very compact overall.

In the beam path of the microscope, there are preferably means to adjust the angle of incidence on the surface of the specimen. It has been determined that the angle of incidence for the measurement of the parameters of polarized light should preferably be in the range of 60° to 80°, whereby angles of 70° are most appropriate. To achieve this, a diaphragm ring is located in front of the lens.

The integration of a micropolarimeter into a microscope has become possible because the micropolarimeter is small and does not contain any rotating components.

The preferred applications are polarization microscopy and the measurement of film thickness.

The polarizer is preferably located between the collimator and the beam splitter, so that the light beams strike the polarizer perpendicularly, as far as possible.

In an additional ellipsometer alternative, the light source is a laser diode array with collimation lenses, whereby this illumination system is combined into one unit with the micropolarimeter claimed by the invention.

BRIEF DESCRIPTION OF THE DRAWINGS

Exemplary embodiments of the invention are explained in greater detail below and are illustrated in the accompanying drawings, in which.

DETAILED DESCRIPTION OF THE INVENTION

Figure 1:
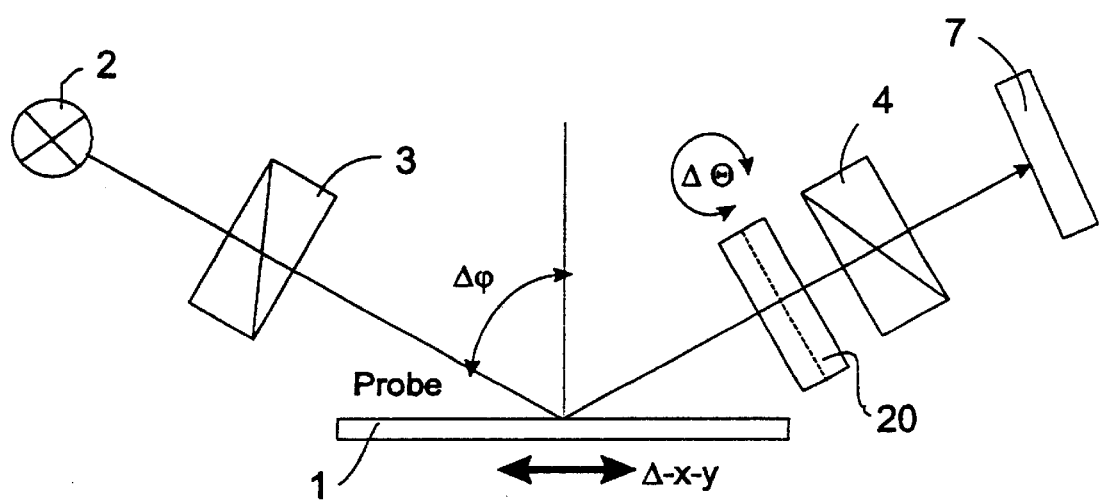
FIG. 1 is a schematic drawing showing the construction of a conventional ellipsometer system.

FIG. 1 is a schematic illustration of an ellipsometer of the prior art. The light emitted by a light source 2 passes a polarizer 3 and strikes the specimen 1, where the light is reflected at the angle Δφ. After passing through a retarder 20 and an analyzer 4, the reflected light strikes a detector 7. The analyzer 4 consists of a stationary analyzer wafer, whereby the retarder in the devices of the prior art can be rotated by the angle ΔΘ. This rotation of the retarder 20 is eliminated by the location of the retarder pixels claimed by the invention in a retarder array, which is described in connection with FIGS. 2 and 3.

Figure 2:
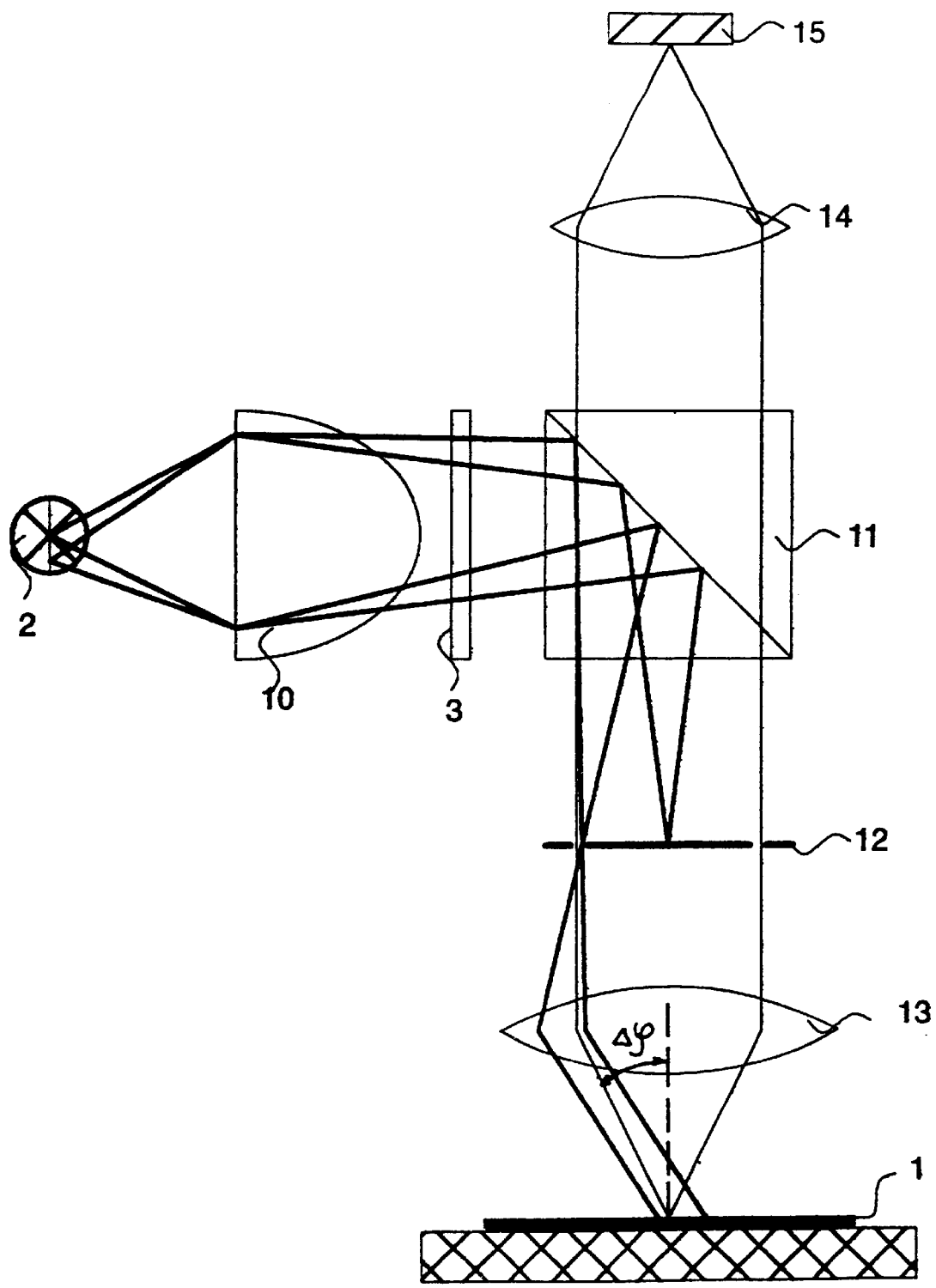
FIG. 2 shows an ellipsometer with a reflected light microscope with an integrated micropolarimeter.
Figure 3A:
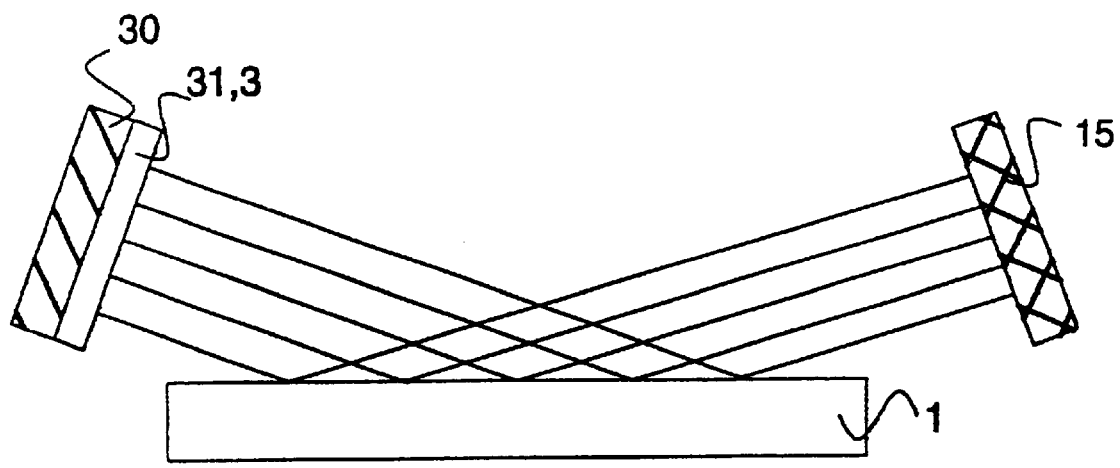
FIGS. 3a, 3b show an additional exemplary embodiment of an ellipsometer.

The ellipsometer arrangements illustrated in FIGS. 2 and 3a are suitable for the guidance of the beam for the imaging of the entire surface of the specimen 1. FIG. 2 shows a reflected light microscope with an integrated micropolarimeter 15, which has a light source 2, a polarizer 3, a collimator 10, a beam splitter 11, an aperture diaphragm 12 which is realized in the form of a diaphragm ring, as well as a lens 13 and an eyepiece 14. The diaphragm ring is realized so that the angle of incidence Δφ is in the range from 60° to 80°. Light beams with other angles of incidence are masked out. By means of the lens 13 and the eyepiece 14, the surface of the specimen is imaged on the micropolarimeter 15 with the retarder array 21, analyzer 4 and detector 7.

Figure 3B:
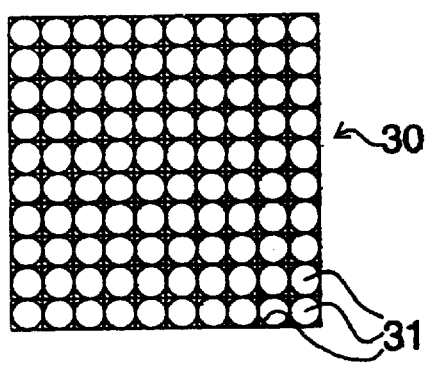

FIG. 3a illustrates an additional alternative of an ellipsometer, which has, as the light source, a laser diode array 30 with collimation lenses 31 and polarizer 3. This device also makes possible a superficial illumination of the specimen 1. FIG. 3b is a plan view of such a laser diode array 30 with collimation lenses 31.

Figure 4A:
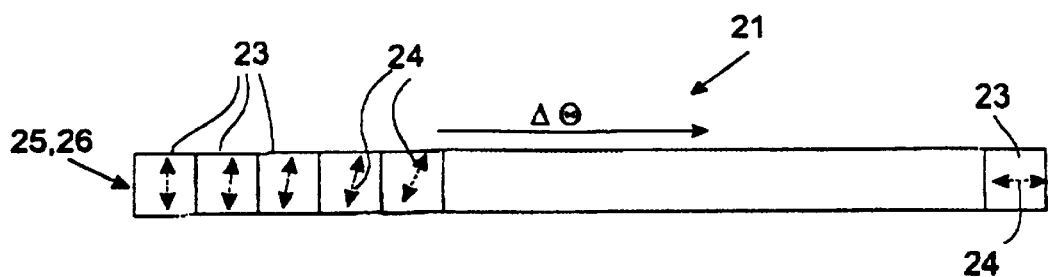
FIGS. 4a, 4b show an exemplary embodiment of an arrangement of retarder pixels.

FIG. 4a illustrates a retarder array 21 in which the pixels 23 are combined in the form of pixel groups 25 into a pixel line 26. The orientations of the major axes 24 of the pixels 23 make a gradual transition from a vertical direction into a horizontal direction. This situation corresponds to the full rotation of a conventional retarder by the angle ΔΘ. If a point of the specimen is imaged on such a retarder array, then the characteristics of the specimen can be determined on this point without rotation of the retarder.

Figure 4B:
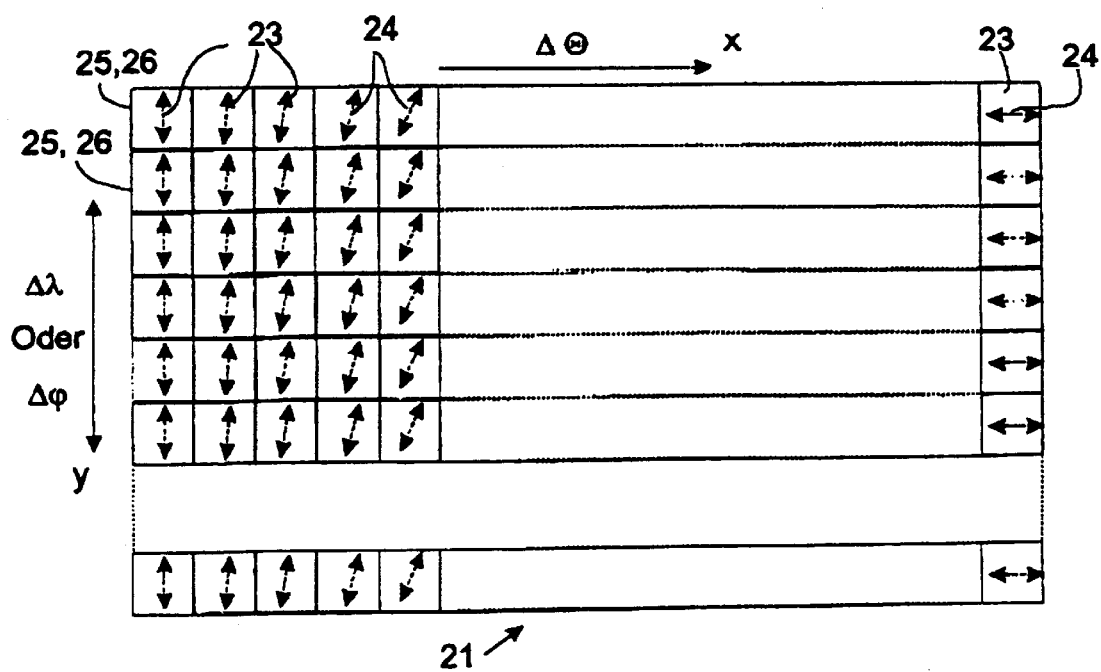

FIG. 4b shows a number of such pixel groups 25 or pixel lines 26 in the form of a matrix. The orientations of the major axes 24 of the retarder pixels 23 in one column are identical. While the X-direction can be used for the polarization analysis, the Y-direction is available for a spectral or angular dispersion. In this manner, the variety of the physical information that can be determined for each specimen point can be increased.

Figure 5A:
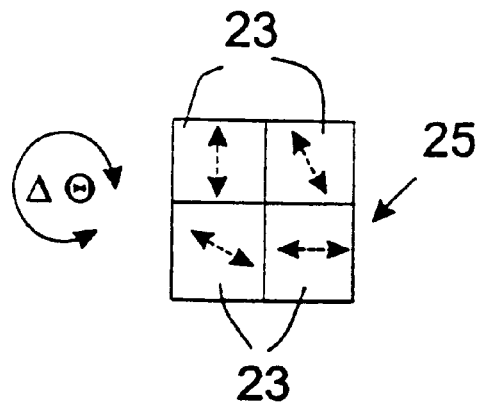
FIGS. 5a, 5b show an additional exemplary embodiment of an arrangement of retarder pixels
Figure 5B:
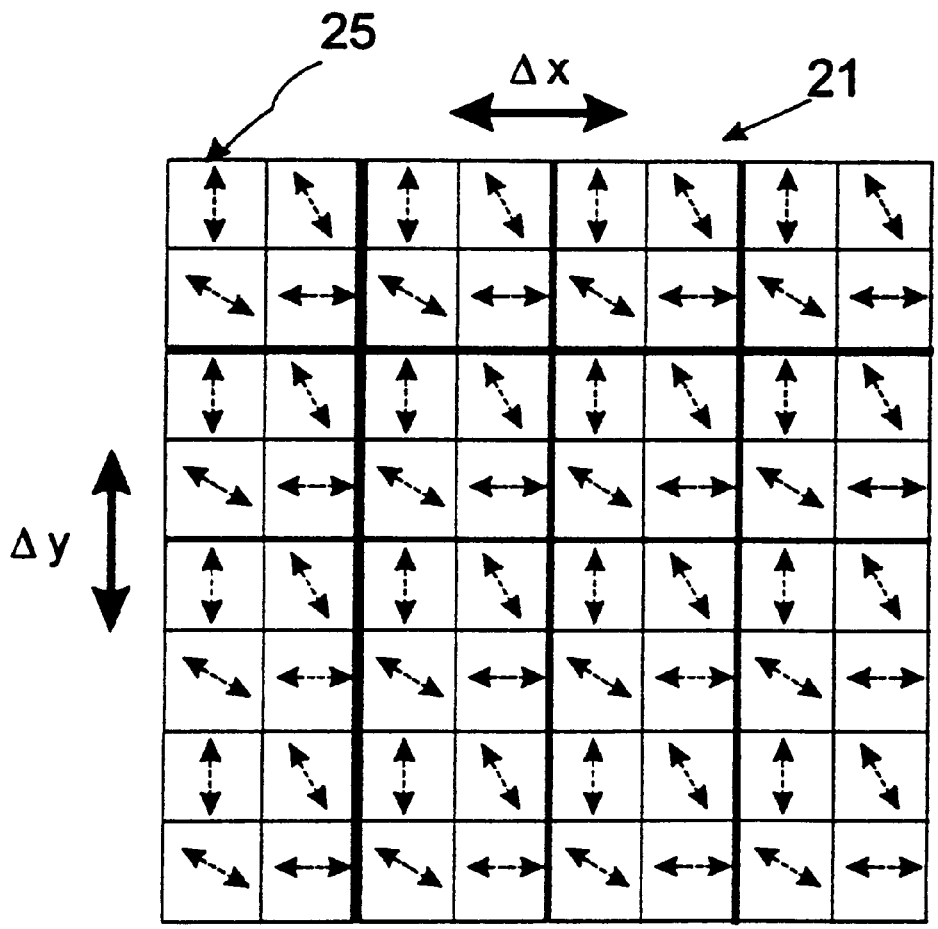

FIG. 5a shows a pixel group 25 that consists of four pixels combined into a compact micropolarimeter. The combination of such pixel groups 25 into a matrix, like the one illustrated in FIG. 5b, provides an image of the optical characteristics of the specimen.

The local resolution of the imaging polarimeter is determined by the dimensions of a pixel group 25. The dimensions of the pixels 23 must be selected so that they cover the area of a pixel of a CCD matrix of approximately 10×10 $\mu m^2$. A group of four pixels 23, for example, the major axes 24 of which are oriented differently, is sufficient to measure the polarization on a surface element of 20×20 $\mu m^2$. A CCD matrix contains up to 4000×4000 pixels. That means that in connection with an upstream polarizer, this device can be used to simultaneously perform an imaging polarization analysis with 200×200 pixels. The film thickness distribution of the structures, e.g. of a circuit on a chip or the distribution of stresses in a pane of glass, in a transparent film or in a fiber, is obtained with the speed and resolution of a CCD camera. The grid dimension of the retarder array 21 and of the detector array are identical. The components are connected to each other so that a clear association between the two arrays is ensured.

Figure 6:
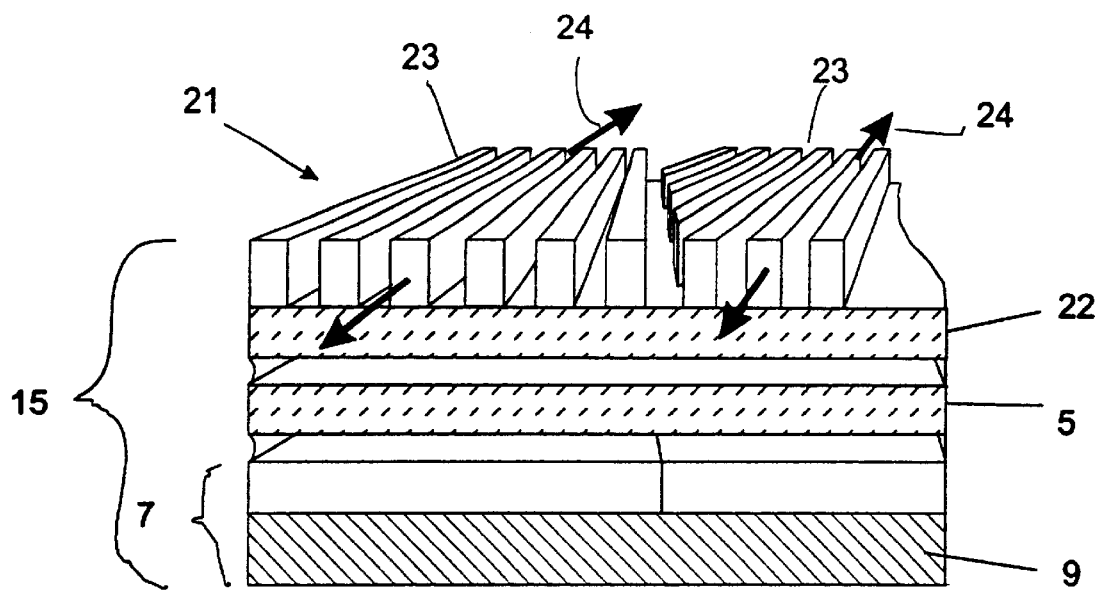
FIG. 6 is a view in perspective of a detail of a pixel group.

FIG. 6 shows a detail of a pixel group 25, whereby two pixels 23 are shown. The pixels 23 are formed by two grids 27, the major axis orientations 24 of which are at different angles. The grid structures 2 are made of a transparent material, and form a unit with the transparent retarder substrate 22. Typical dimensions of such grid structures are: width 200 mm, trench width 200 mm, depth 400 mm. When light falls on these structures, the surface reacts like an artificially generated anisotropic material, similar to the anisotropic crystals used in conventional optics for the manufacture of retarders.

These grids of the pixels 23 can be manufactured by means of electron beam lithography in combination with ion beam etching processes. After the manufacture of the grid 27, the grid substrate unit is connected by means of an adhesive with the analyzer 5, and the latter is in turn connected with the CCD detector 7, which has a substrate 9 on which the CCD pixels are located. The position of the axis of the analyzer 5 is selected so that it does not coincide with one of the major axes 24 of the retarder 23. This becomes possible if the angles of the major axes 24 within a pixel group vary by 30°, while the axis of the analyzer 5 is at 45°.

Figure 7:
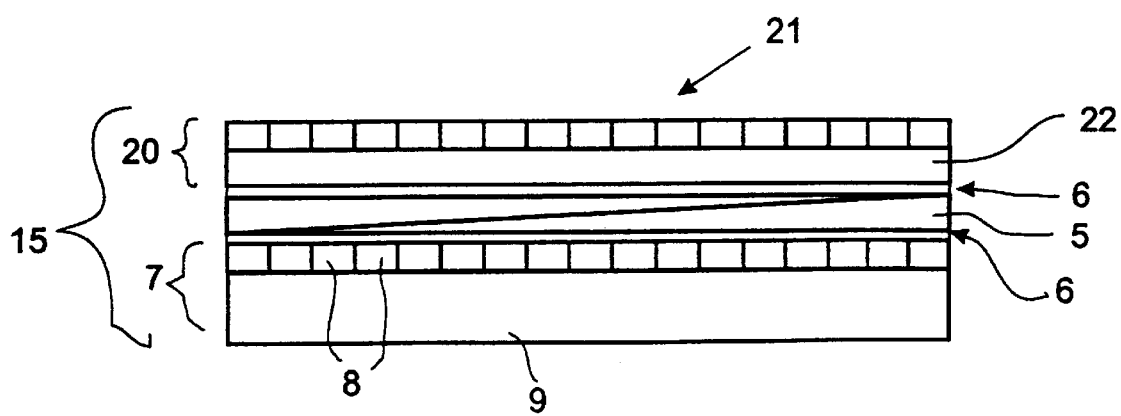
FIG. 7 is a vertical section through a detector.

FIG. 7 shows a vertical section through a micropolarimeter 15 with analyzer wafer 5, retarder array 21 and detector 7.

What is claimed is:

1. A micropolarimeter comprising:
a non-rotating retarder, an analyzer disc located downstream from said retarder and a photo-detector matrix, said retarder comprising a one-piece retarder array with at least one pixel group that has at least three pixels, said pixels having major axis orientations which are distributed over an angular range of 360°, and said pixels being made of dielectric grid structures with grid intervals that are adapted to be less than the wavelength of light being used.

2. A micropolarimeter according to claim 1, wherein the pixels of said pixel group are located in at least one pixel line.

3. A micropolarimeter according to claim 1, wherein the retarder array has a pixel matrix with identical pixel lines.

4. A micropolarimeter according to claim 3, wherein a prism or a grid for wavelength selection is located between a specimen and the retarder array.

5. A micropolarimeter according to claim 1, wherein the pixels of a pixel group are arranged two-dimensionally.

6. A micropolarimeter according to claim 1, further including detector pixels having a size equal to the size of the retarder array pixels.

7. A micropolarimeter according to claim 1, wherein the pixels of the retarder array are located on a common substrate.

8. A micropolarimeter according to claim 1, wherein the retarder array is glued onto an analyzer wafer.

9. A micropolarimeter according to claim 8, wherein analyzer wafer is glued onto the photo-detector matrix.

10. A micropolarimeter according to claim 1, wherein the retarder array is manufactured by means of lithographic, embossing or injection molding methods.

11. An ellipsometer comprising:
a light source, a polarizer, a polarimeter and a reflected light microscope with a lens and an eyepiece, whereby the polarizer and polarimeter are integrated into the reflected light microscope, said polarimeter being a micropolarimeter comprising a non-rotating retarder, an analyzer disc located downstream from said retarder and a photo-detector matrix, whereby the retarder is a one-piece retarder array with at least one pixel group that has at least three pixels, said pixels having major axis orientations which are distributed over an angular range of 360°, said micropolarimeter being integrated into the focal plane of the eyepiece, and said pixels being made of dielectric grid structures with grid intervals that are adapted to be less than the wavelength of light being used.

12. An ellipsometer according to claim 11, wherein in the beam path of the microscope there are means to adjust the angle of incidence on a surface of a specimen.

13. An ellipsometer according to claim 11, wherein an aperture diaphragm is located in front of the lens.

14. An ellipsometer according to claim 11, wherein the polarizer is located between a collimator and a beam splitter of the microscope.

15. An ellipsometer comprising:

a light source, a polarizer and a polarimeter, said light source being a laser diode array with collimation lenses, said polarimeter being a micropolarimeter comprising a non-rotating retarder, an analyzer disc located downstream of said retarder, and a photo-detector matrix, whereby the retarder is a one-piece retarder array with at least one pixel group that has at least three pixels, said pixels having orientations which are distributed over an angular range of 360°, and said pixels being made of dielectric grid structures with grid intervals that are adapted to be less than the wavelength of light being used.

* * * * *